United States Patent
Choi et al.

(10) Patent No.: US 11,690,737 B2
(45) Date of Patent: Jul. 4, 2023

(54) STENT USING WIRELESS TRANSMITTED POWER AND EXTERNAL OPERATING APPARATUS THEREOF

(71) Applicant: THE CATHOLIC UNIVERSITY OF KOREA INDUSTRY-ACADEMIC COOPERATION FOUNDATION, Seoul (KR)

(72) Inventors: Myung-Gyu Choi, Seoul (KR); Seok-Hyun Yun, Belmont, MA (US); Bo-In Lee, Seoul (KR); Jae Myung Park, Seoul (KR); Ehsan Kamrani, Waterloo (CA); Ali Kemal Yetisen, Peabody, MA (US)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 16/328,094

(22) PCT Filed: Sep. 5, 2016

(86) PCT No.: PCT/KR2016/009884
§ 371 (c)(1),
(2) Date: Feb. 25, 2019

(87) PCT Pub. No.: WO2018/038304
PCT Pub. Date: Mar. 1, 2018

(65) Prior Publication Data
US 2019/0183665 A1  Jun. 20, 2019

(30) Foreign Application Priority Data
Aug. 26, 2016 (KR) .......................... 10-2016-0109264

(51) Int. Cl.
*A61F 2/82* (2013.01)
*A61F 7/12* (2006.01)
(Continued)

(52) U.S. Cl.
CPC ................ *A61F 2/82* (2013.01); *A61B 5/076* (2013.01); *A61B 5/6862* (2013.01);
(Continued)

(58) Field of Classification Search
CPC ................................................. A61F 2007/126
See application file for complete search history.

(56) References Cited

U.S. PATENT DOCUMENTS 5,360,440 A * 11/1994 Andersen ................. A61N 1/05
607/75
5,980,565 A * 11/1999 Jayaraman ................ A61F 2/07
623/1.12
(Continued)

FOREIGN PATENT DOCUMENTS

KR  1020120015133 A  2/2012
KR  1020120015173 A  2/2012
(Continued)

*Primary Examiner* — Jacqueline Woznicki
(74) *Attorney, Agent, or Firm* — Hoffman & Baron, LLP (57) ABSTRACT

A stent device including a stent coated with a photosensitizer, the stent including a pair of electrodes; and a circuit fixed to the stent, the circuit including a light emitting diode, a power receiving means for wirelessly receiving power from the outside, and converting the power to electric power; a second communicating means for receiving a control command from the outside; and a second control means for applying, based on the control command, the electric power to the electrodes causing an electric current to flow through the stent between the electrodes, the flow causing heating of the stent, and for controlling a temperature of the stent to provide hyperthermia therapy to a tumor, the second control means further for applying, based on the
(Continued)

control command, the electric power to the light emitting diode to emit a predetermined wavelength of light to the photosensitizer to provide photodynamic therapy to the tumor.

2 Claims, 7 Drawing Sheets

(51) Int. Cl.

| | | |
|---|---|---|
| A61B 5/07 | (2006.01) | |
| A61B 18/00 | (2006.01) | |
| A61F 2/48 | (2006.01) | |
| A61F 7/00 | (2006.01) | |
| A61B 18/10 | (2006.01) | |
| A61B 18/08 | (2006.01) | |
| A61N 5/06 | (2006.01) | |
| A61B 5/00 | (2006.01) | |
| A61N 1/372 | (2006.01) | |
| A61N 1/378 | (2006.01) | |
| A61B 5/1473 | (2006.01) | |

(52) U.S. Cl.
CPC ............ *A61B 18/082* (2013.01); *A61B 18/10* (2013.01); *A61F 7/12* (2013.01); *A61N 1/3787* (2013.01); *A61N 1/37223* (2013.01); *A61N 5/0601* (2013.01); *A61N 5/062* (2013.01); *A61N 5/0603* (2013.01); *A61B 5/1473* (2013.01); *A61B 2018/00577* (2013.01); *A61F 2/482* (2021.08); *A61F 2007/0094* (2013.01); *A61F 2007/126* (2013.01); *A61F 2250/0001* (2013.01); *A61N 2005/0602* (2013.01); *A61N 2005/0651* (2013.01)

(56) References Cited

U.S. PATENT DOCUMENTS

| | | | | |
|---|---|---|---|---|
| 6,206,914 B1* | 3/2001 | Soykan | ............... | A61F 2/02 604/891.1 |
| 6,245,100 B1* | 6/2001 | Davila | ............... | A61F 2/91 606/198 |
| 6,423,056 B1* | 7/2002 | Ishikawa | ............ | A61N 1/406 607/113 |
| 6,808,535 B1* | 10/2004 | Jordan | .............. | A61L 31/028 623/1.34 |
| 9,011,329 B2* | 4/2015 | Ferren | .............. | A61B 5/14546 600/529 |
| 9,198,563 B2* | 12/2015 | Ferren | .............. | A61B 1/041 |
| 2004/0106841 A1* | 6/2004 | Shaw | ................. | A61N 5/1002 604/890.1 |
| 2006/0079740 A1* | 4/2006 | Silver | ................ | A61B 5/6882 600/353 |
| 2006/0173514 A1* | 8/2006 | Biel | .................... | A61K 9/703 607/88 |
| 2009/0093728 A1* | 4/2009 | Hyde | ................. | A61B 5/061 606/41 |
| 2009/0163965 A1* | 6/2009 | Boyden | .............. | A61L 2/14 607/3 |
| 2009/0299359 A1* | 12/2009 | Swain | ................ | A61B 18/12 606/27 |
| 2010/0100160 A1* | 4/2010 | Edman | ............... | A61B 5/444 607/88 |
| 2010/0174346 A1* | 7/2010 | Boyden | .............. | A61F 2/30 607/113 |
| 2010/0228234 A1* | 9/2010 | Hyde | ................ | A61M 1/3683 604/891.1 |
| 2010/0234793 A1* | 9/2010 | Dacey, Jr. | .......... | A61B 5/14546 604/8 |
| 2011/0022151 A1* | 1/2011 | Shin | .................. | A61F 2/04 623/1.11 |
| 2011/0144566 A1* | 6/2011 | Dacey, Jr. | ............ | A61F 2/30 604/21 |
| 2011/0152750 A1* | 6/2011 | Dacey, Jr. | ............ | A61F 2/30 604/21 |
| 2011/0152752 A1* | 6/2011 | Dacey, Jr. | ........... | A61M 27/002 604/21 |
| 2011/0152789 A1* | 6/2011 | Dacey, Jr. | ............ | A61F 2/30 422/1 |
| 2011/0152790 A1* | 6/2011 | Dacey, Jr. | ............ | A61F 2/30 604/264 |
| 2011/0160643 A1* | 6/2011 | Dacey, Jr. | ............ | A61L 2/00 604/21 |
| 2011/0160644 A1* | 6/2011 | Dacey, Jr. | ............ | A61L 2/0011 604/21 |
| 2012/0253449 A1* | 10/2012 | Chang | ............... | A61N 5/062 623/1.15 |
| 2013/0192611 A1* | 8/2013 | Taepke, II | ......... | A61N 1/37518 128/898 |
| 2015/0134044 A1* | 5/2015 | Kim | .................. | A61B 18/14 623/1.16 |
| 2015/0335285 A1 | 11/2015 | Poon et al. | | |
| 2016/0000590 A1 | 1/2016 | Boyden et al. | | |

FOREIGN PATENT DOCUMENTS

| | | |
|---|---|---|
| KR | 1020140099209 A | 8/2014 |
| KR | 1020160054659 A | 5/2016 |

\* cited by examiner

STENT USING WIRELESS TRANSMITTED POWER AND EXTERNAL OPERATING APPARATUS THEREOF

CROSS-REFERENCE TO RELATED APPLICATION

The present application in the U.S. National Phase of PCT/KR2016/009884, filed on Sep. 5, 2016, which claims priority to Korean Patent Application No. 10-2016-0109264, filed on Aug. 26, 2016, the entire contents of which are incorporated herein by reference.

BACKGROUND

Technical Field

The present invention is related to a medical stent. In particular, the present invention is related to a stent using wirelessly transmitted power and an external driving apparatus thereof.

Related Art

Figure 8:
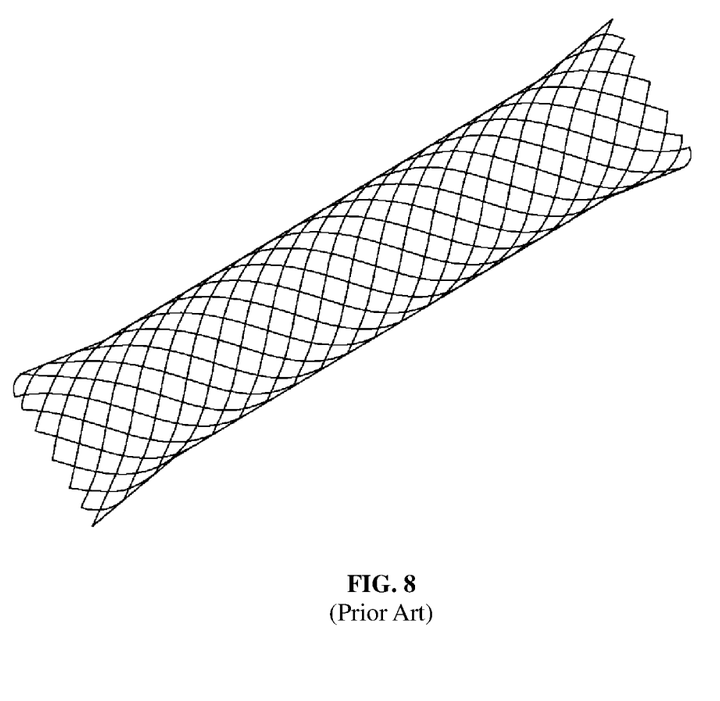
FIG. 8 is a plan view of a conventional stent.

FIG. 8 is a top plan view of a conventional medical stent. As shown in FIG. 8, a self-expanding metal stent using a shape memory alloy has been widely used in the therapy of blockages in blood vessels, digestive canals, etcetera. The stent expands the interior of a passageway by physical force, allowing preventing the passageway from a blockage and also restoring the flow of blood or other fluids. Further, the stent is shrunk either when placed in the exterior or while being inserted, allowing reducing the external diameter thereof. Alternatively, the stent is expanded depending on the temperature when placed in a surgical position, allowing increasing the external diameter thereof. Therefore, the conventional stent, as shown in FIG. 8, has either a cylindrical mesh shape or a cylindrical net shape using metal wires.

However, the conventional stent has only a function to expand by mechanical force the interior of blood vessels or digestive canals, which have become narrow depending on the tumor proliferation, but is irrelevant to the active therapy such as anticancer therapy. Thus, there are drawbacks that a tumor proliferates in openings of the mesh (or net), resulting in the blockage. A polymer coated stent is provided so as to prevent such drawbacks. However, the stent is restrictively used because of the drawback that the stent is detached from the original position by gastrointestinal peristalsis.

Meanwhile, various conventional anticancer therapies, such as hyperthermia, photodynamic therapy, anticancer drug delivery, etc., are performed separately or in combination with each other. However, according to such conventional anticancer therapies, a surgical instrument should have approached a tumor. Also, wiring or piping for signals, power, and drugs should have been connected with wires. Thus, there are drawbacks that a patient cannot be provided with continuous anticancer therapy and suffers from much pain and inconvenience.

SUMMARY

Therefore, the present invention is provided to overcome the aforementioned drawbacks. The present invention is directed to providing a stent using wirelessly transmitted power and an external driving apparatus thereof, wherein the power is wirelessly transmitted to a stent inserted into the human body, allowing performing the original function of the stent as well as anticancer therapy.

Further, the present invention is directed to a stent using wirelessly transmitted power and an external driving apparatus thereof, wherein a sensor detects and transmits various physiological states of a tumor and the surroundings thereof to the exterior, allowing monitoring a state of the tumor in real time.

According to the first aspect of the present invention, a stent using wirelessly transmitted power includes a power receiving portion 230 which wirelessly receives power from the exterior, wherein the stent is a heating stent 250, allowing heating using the power.

According to another aspect of the present invention, the stent further includes a power storage portion 240 which stores the power between the power receiving portion 230 and the heating stent 250.

According to another aspect of the present invention, the stent further includes: a second communication part 270 which receives a control command from the exterior; and a second control portion 210 which controls the heating stent 250 based on the control command.

According to another aspect of the present invention, the stent further includes an electrical stimulation portion 290 which generates electrical stimulation using the power, wherein the electrical stimulation 290 applies the generated electrical stimulation to the heating stent 250.

According to another aspect of the present invention, the stent further includes: a photosensitizer which is coated on the heating stent 250; and an LED 220 which emits light to the surroundings of the heating stent 250, wherein the second control portion 210 controls the LED 220 based on the control command.

According to another aspect of the present invention, the stent further includes a sensor 260 which measures a biochemical environment of the surroundings of the heating stent 250, wherein the second control portion 210 transmits an output of the sensor 260 to the exterior through the second communication portion 270.

According to another aspect of the present invention, at least one of the power receiving portion 230, the power storage portion 240, the second communication portion 270, the second control portion 210, and the electrical stimulation portion 290 is coated with a nontoxic silicone layer 280 or Teflon.

According to another aspect of the present, the silicone layer 280 or the Teflon is placed on an inner or outer surface of the heating stent 250 or in a mid-point of a cross-sectional surface thereof.

According to the second aspect of the present invention, an external operating apparatus of the stent using wirelessly transmitted power includes: a first communication portion 150 which is capable of wirelessly communicating with the second communication portion 270; an RF signal generation portion 110 which generates the power and an RF amplification portion 120; a power transmission portion 130 which wirelessly transmits the amplified power to the power receiving portion 230; and a first control portion 100 which controls the first communication portion 150 and the RF signal generation portion 110.

According to one example embodiment of the present invention, it is possible to wirelessly transfer power to a stent inserted into the human body, thereby performing anticancer therapy continuously. Further, it is possible to inhibit tumor proliferation, thereby preventing detachment of the stent or a blockage of the internal cavity.

In using a heating stent, it is possible to select a therapy such as hyperthermia therapy, photodynamic therapy, electrical stimulation, etc., easily from the exterior, thereby performing a variety of anticancer therapies according to the circumstance of a patient.

In addition, various sensors can be mounted on a circuit portion, thereby detecting and transmitting various physiological states of a tumor and the surroundings thereof to the exterior in real time.

BRIEF DESCRIPTION OF THE DRAWINGS

The foregoing features of the present invention will become more fully apparent from the following description, taken in conjunction with the accompanying drawings. Understanding that these drawings depict only typical embodiments of the invention and are, therefore, not to be considered limiting of its scope, the invention will be described with additional specificity and detail through use of the accompanying drawings in which.

DETAILED DESCRIPTION

The above and other features, objects and advantages of the present invention will now be more clearly understood from the following preferred example embodiments with the accompanying drawings. However, the present invention is not limited to the example embodiments set forth herein and may be embodied in many different forms. Rather, these embodiments are provided so that this invention will be thorough and complete, and will fully convey the scope of the invention to those skilled in the art.

It will be understood that the terms, such as 'comprises' and/or 'comprising', are intended to designate described features, numbers, steps, operations, elements, parts, or combinations thereof, but do not preclude the presence or addition of one or more features, numbers, steps, operations, elements, parts, or combinations thereof.

Unless otherwise defined, all terms used herein have the same meaning as commonly understood by one of ordinary skill in the art to which the present disclosure relates. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
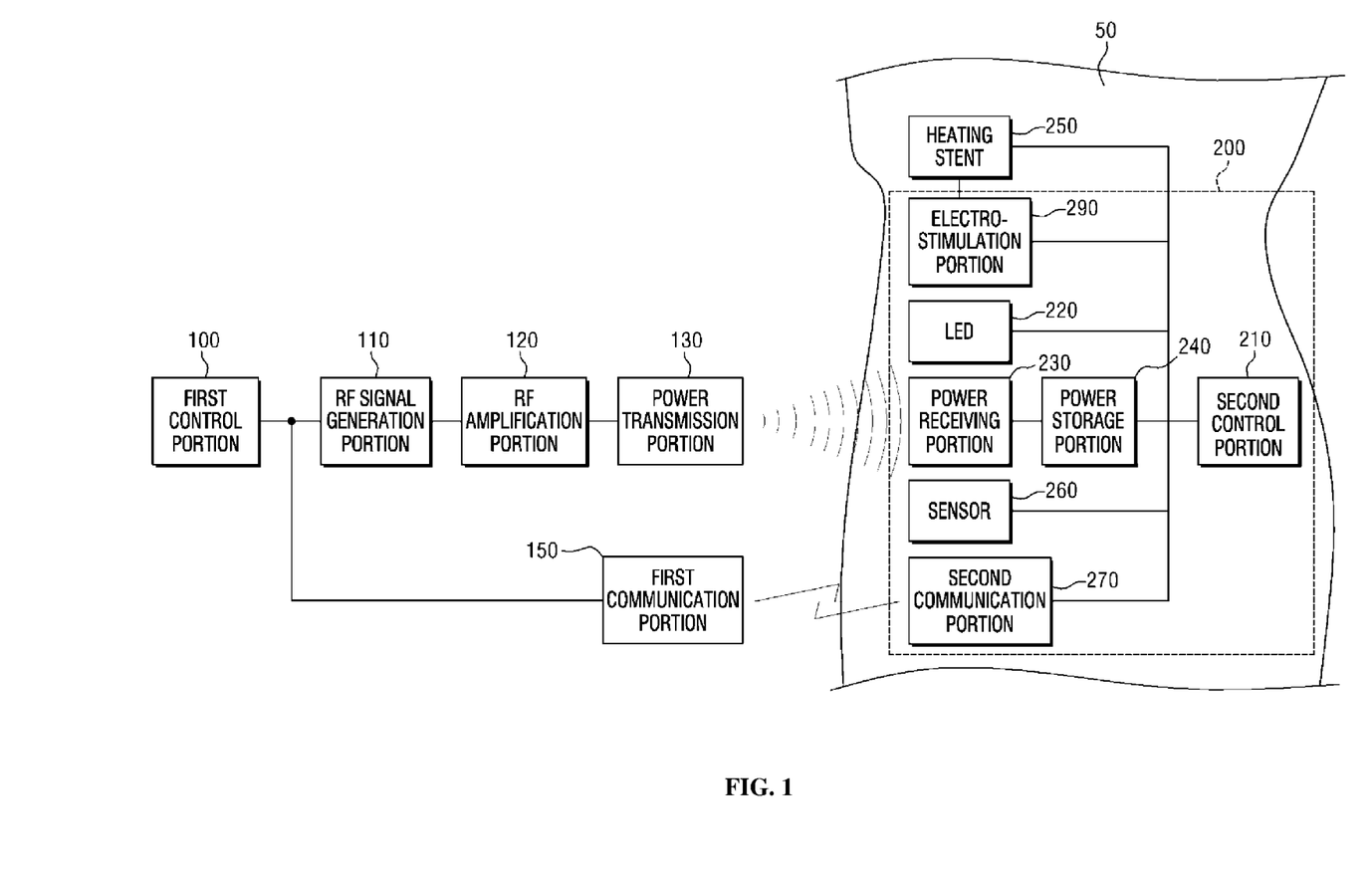
FIG. 1 is a schematic block diagram of a stent using wirelessly transmitted power and an external operating apparatus thereof according to one example embodiment of the present invention.

FIG. 1 is a schematic block diagram of a stent using wirelessly transmitted power and an external operating apparatus thereof according to one example embodiment of the present invention. As shown in FIG. 1, the stent inserted into a tube may include a heating stent 250 and a circuit portion 200.

The heating stent 250 may be coupled with a second control portion 210 and a power storage portion 240. The heating stent may generate heat according to a control operation of the second control portion 210, allowing transferring the heat to the surroundings thereof. That is, electrodes may be coupled to both ends of the heating stent 250, allowing applying an electric current. Thus, the heating stent 250, as a resistor, may function like a heater. The heating stent 250 is adapted for hyperthermia therapy.

Figure 6A:
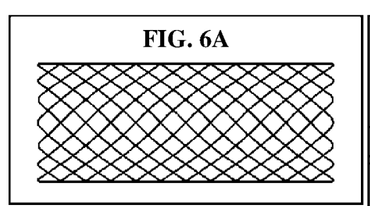
FIGS. 6A-6F show photographs of a heating stent according to one example embodiment of the present invention and of various heating experiments.
Figure 6B:
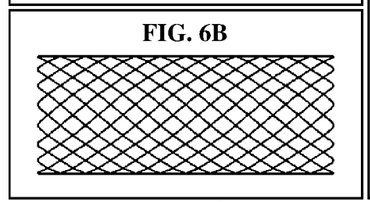
Figure 6C:
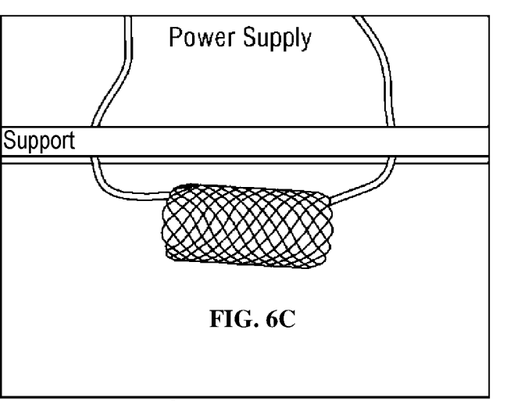

The therapeutic effect of Hyperthermia Therapy (hereinafter, referred to as HTT) has been undervalued because it is impossible to transfer a heat of high temperature, i.e., 42° C. or above (particularly, 45° C.-50° C.) to the tumor area. Such temperatures are well known to be the most effective for killing the cancer cell. The aforesaid underestimate results from technical problems and circumstances around the tumor area. Meanwhile, there is an academic report that cancer can be reduced merely by increasing the temperature of a tumor to 40° C.-41° C., enough that immune cells can be activated by action of the heat. Accordingly, the heating stent 250 of the present invention may reach the tumor directly, allowing increasing therapeutic effects of HTT. Further, the heating stent may control the temperature in real time according to patient's feeling or suspend HTT, allowing increasing convenience. Examples of the heating stent 250 are shown in FIGS. 6A-6C.

The circuit portion 200 may be equipped with an electrical stimulation portion 290, an LED 220, a power receiving portion 230, a power storage portion 240, a second control portion 210, a sensor 260, a second communication portion 270, etcetera.

The electrical stimulation 290 may be coupled with the heating stent 250 and the second control portion 210 and the power storage portion 240. The electrical stimulation portion 290 may convert the power stored in the power storage portion 240 into electrical stimulation (electric shockwave) according to control action of the second control portion 210. The electrical stimulation portion 250 may transfer the converted electrical stimulation to the stent 250. The metal stent 250 may transfer the transferred electrical stimulation to the tumor and surrounding tissues thereof, allowing performing electrical stimulation therapy. The second control portion 210 may command the amplitude, duration, and pulse rate of the electrical stimulation on the basis of the external command transmitted to the second communication portion.

The LED 220 may be coupled to the power storage portion 240 and the second control portion 210 and may emit a predetermined wavelength of light. The LED 220 is adapted for PhotoDynamic Therapy (hereinafter, referred to as PDT), and thus the surface of the stent 250 is coated with photosensitizer. The PDT is a form of phototherapy to apply a photosensitizer sensitive to light onto a region to be treated, followed by irradiating a particular wavelength of light thereto, allowing accumulating the light selectively on the diseased cell. The light energy which reaches the photosensitizer-absorbing tumor or the lesion may facilitate the generation of active oxygen in the relevant cell, allowing destroying the cell. Particularly, the stent set in the body is not limited to the duration of irradiation of the LED 220.

The photosensitizer coated on the surface of the stent 250 is a medicament to be administered into a person suspected to have a malignant tumor for the purpose of diagnosis of early cancer and premalignant, and of cancer therapy. The photosensitizer has no effect on the diagnosis or treatment of cancers when used alone but traces the cancer, allowing accumulating in a high concentration within a cancer cell. Thus, if irradiating a particular wavelength of light to a region suspected as a cancer, strong fluorescence may be emitted, allowing selective necrosis of the cancer tissue.

The photosensitizer may include, as an example, a hemato-porphyrine derivative, aminolevulinic acid, chlorin, etc., especially Photgem and Phtofrin as a product. Administration method thereof may include intravenous injection, drinking, nasal inhalation, dermal application, spraying, direct administration to the bladder or the uterus, etcetera. According to the conventional PDT, a light source should approach the tumor accompanying a wire. Thus, the conventional PDT has a slightly high effect on only superficial cancers in which the light source is capable of reaching the cancer cell by the endoscope from the exterior through bronchial tubes or gullet. On the other hand, the PDT using the stent 250 according to the present invention has the advantage of application to every position where the stent 250 can be inserted.

The power receiving portion 230 may wirelessly receive RF power transmitted from a power transmission portion 130 that is approximately 2 cm-3 cm apart from the exterior of the body 50, allowing conversion of the RF power to electric power.

The power storage portion 240 may be coupled between the power receiving portion 230 and the second control portion 210, allowing storing the electric power output from the power receiving portion 230. The power storage portion 240 may be adapted to output stable electric power or, if necessary, high power. The power storage portion 240 may include, as an example, a condenser, a capacitor, a secondary battery, etcetera.

The sensor 260 may be coupled with the second control portion 210, and may detect a variety of physiological signals in the region where the stent 250 is inserted, followed by transmitting such detected signals to the exterior through the second communication portion 270. The sensor 260 may include, as an example, a temperature sensor, a pressure sensor for detecting flow, a pressure sensor using impedance or piezoelectricity for detecting a blockage or detachment, an electromagnetic sensor, a resonant sensor, etcetera.

The second communication portion 270 may be coupled with the second control portion 210, and is capable of bi-directional wireless communication with a first communication portion 150. The second communication 270 may receive a control command from the exterior, allowing transferring the received command to the second control portion 210, and may transmit an output of the sensor 260, the state of each electronic circuit within the circuit portion 200 or outputs thereof to the exterior through the second control portion 210. If the second communication portion 270 may be adapted for near field communication, it is possible to apply any types including, as a principle example, ZigBee, Bluetooth, Wi-Fi, LAN, etcetera.

The second control portion 210 may be electrically coupled with the heating stent 250, the electrical stimulation portion 290, the LED 220, the power storage portion 240, the sensor 260, and the second communication 270. The second control portion 210 may include as a prime example, Micom (microcontroller).

Hereinbefore, described are the respective modules (for example, the electrical stimulation portion 290, the LED 220, the power receiving portion 230, the power storage portion 240, the second control portion 210, the sensor 260, the second communication 270) equipped within the circuit portion 200. However, it is not necessary to have all of such respective modules. It may be possible to omit a part of any such modules or merge together, if necessary in a view of design. For example, if modulating a control signal, followed by incorporation into a wireless power signal (similar to power line modem), the power receiving portion and the second communication portion 270 may be merged together. Further, the LED 220 may be replaced with a laser light source. The heating stent 250 may be coated with an anticancer agent replacing, or together with, the coated photosensitizer.

Hereinafter, described is the configuration of an external operating apparatus for operating the circuit portion 200 from the exterior of the body 50.

A first control portion 100 may be coupled with an RF signal generation portion 110 and a first communication portion 150, and may have a function of monitoring except the coupled modules. The first control portion 100 may be, as a prime example, a notebook computer or a personal computer.

The RF signal generation portion 110 may be coupled between the first control portion 100 and an RF amplification portion 120, and may generate RF signal according to the first control portion.

The RF amplification portion 120 may be coupled between the RF signal generation portion 110 and a power transmission portion 130, and may have a function of amplifying the RF signal output from the RF signal generation portion 110 to a predetermined output.

The power transmission portion 130 may be coupled with the RF amplification portion 120, and may have a function of wirelessly transmitting the RF signal amplified to a predetermined output. The power transmission portion 130 may be, as a principle example, an induction coil which is 2 cm-3 cm apart from the body 50.

The first communication portion 150 may be coupled with the first control portion 100. The first communication portion 150 may wirelessly transmit a control command to the second communication portion 270 according to a control command of the first control portion 100, or may wirelessly receive the output of the second communication portion 270. Further, the first communication portion 150 may maintain the same communication protocol as that of the second communication portion 270, e.g., ZigBee, Bluetooth, Wi-Fi, LAN, etcetera.

Figure 2A:
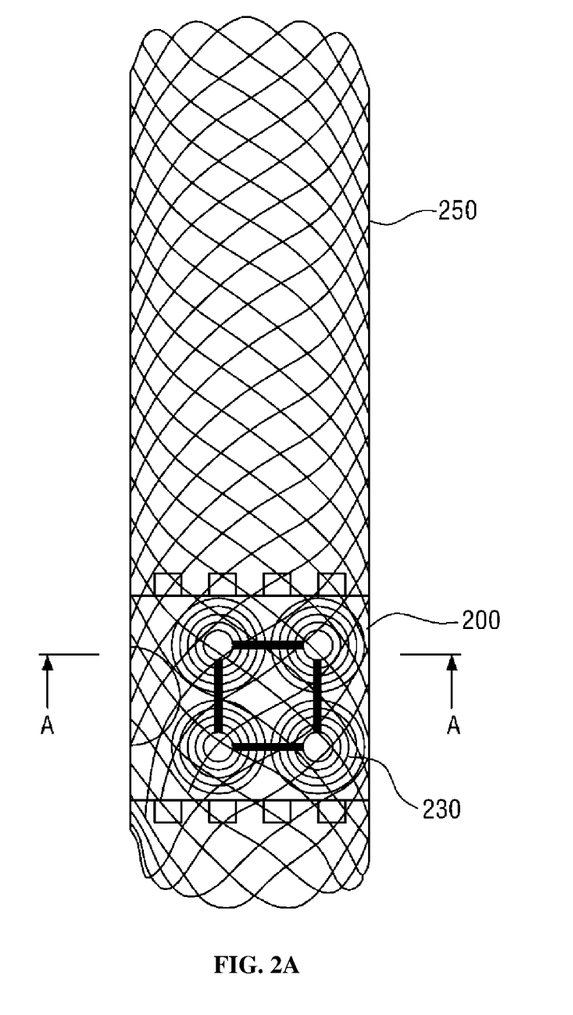
FIG. 2A is a front view of a stent according to a first example embodiment of the present invention, wherein a circuit portion is placed in the interior thereof.
Figure 3:
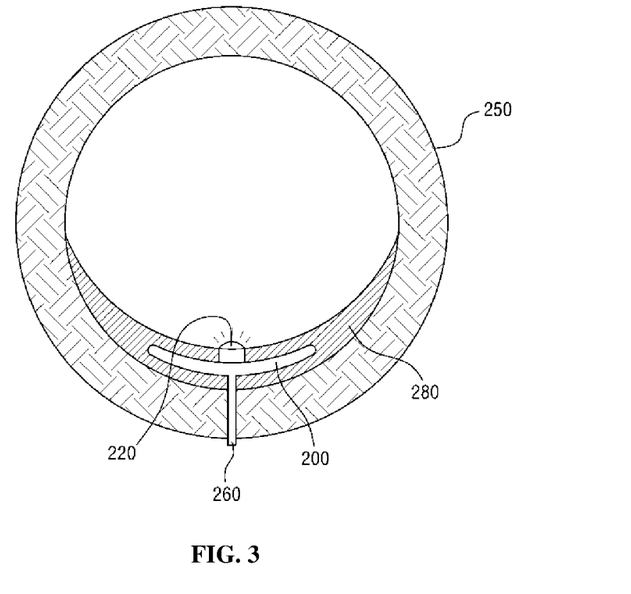
FIG. 3 is a cross-sectional view of an A-A part in FIG. 2A.

FIG. 2A is a front view of a stent according to a first example embodiment of the present invention, wherein a circuit portion 200 may be placed in the interior thereof. FIG. 3 is a cross-sectional view of an A-A part in FIG. 2A. As shown in FIG. 2A and FIG. 3, the circuit portion 200 may be placed on the inner surface of one side of the stent 250. The circuit portion 200 may be embodied into an Application Specific Integrated Circuit (ASIC), a Micro Electro Mechanical System (MEMS), a One Chip, or etcetera. A silicone layer 280 may be a coating layer which surrounds the circuit portion 200, allowing protecting the circuit portion 200 from electric short or corrosion and preventing the outflow of harmful substances from the circuit portion 200. Further, the silicone layer 280 may fix the circuit portion 200 and the stent 250 firmly, allowing preventing detachment of the circuit portion 200. The power receiving portion 230 may be a plurality of induction coils (having a diameter of 1 cm-2 cm) which are connected parallel. The LED 220 may exposed to the exterior of the silicone layer 280, so as to emit light. The sensor 260 may be slightly exposed to the exterior of the silicone layer 280 and/or the stent 250, so as to detect an accurate signal. The silicone layer 280 may be replaced with other materials which are capable of protecting the circuit portion 200 and maintaining the fixability. Such materials may include, as an example, Teflon, Polyimide (PI), polytetrafluoroethylene (PTFE), zwitterionic polymers, siloxanes, polystyrene, polyolefins, fluoropolymers, polyaramid, polycarbonates, acrylic polymers, methacrylates, styrenes and substituted styrenes, polysulfones, epoxies, polyacrylonitriles, polyamides, polyimides, polyvinyl chloride, polyvinylidene chloride, polyvinyl acetals, polyesters, polyvinyl esters, polyesters, polyvinyl ethers, polydiacetylenes, polyvinyl acetate, polyethylene terephthalate and polyethylene oxide, optionally copolymerized with other polymerizable monomers or cross-linkers, covalently crosslinked PEG or acrylamide combined with ionically crosslinked alginate, etcetera.

Figure 2B:
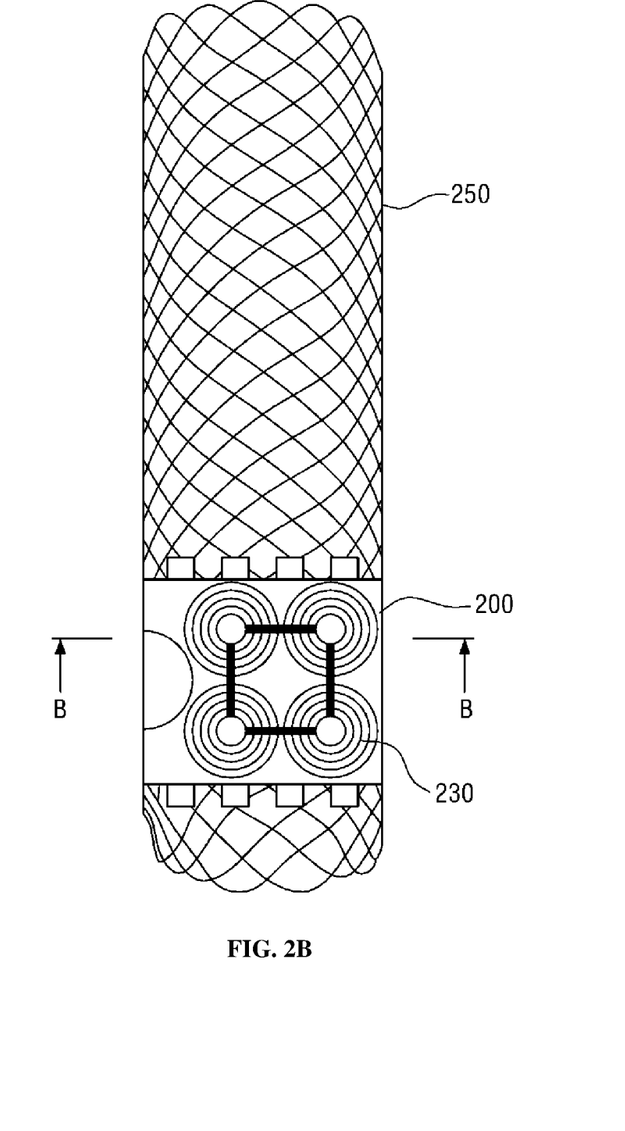
FIG. 2B is a front view of a stent according to a second example embodiment of the present invention, wherein a circuit portion is placed in the exterior thereof.
Figure 4:
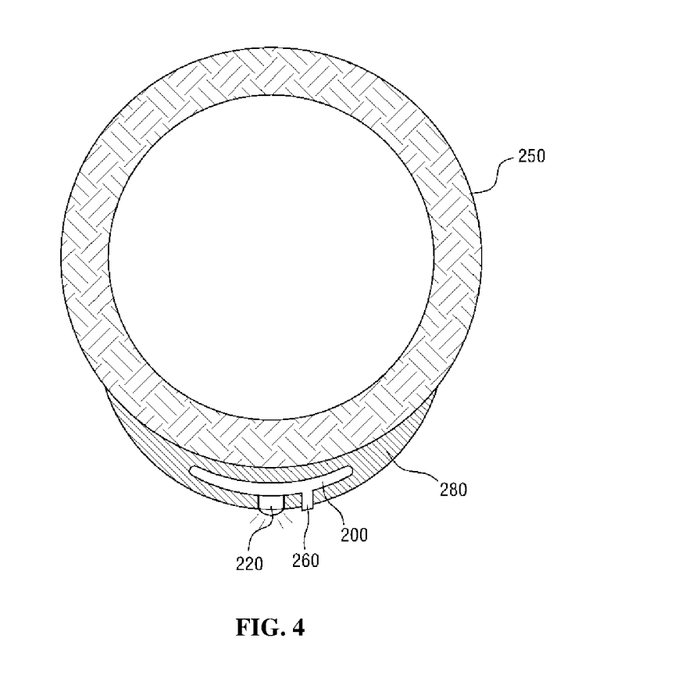
FIG. 4 is a cross-sectional view of a B-B part in FIG. 2B.

FIG. 2B is a front view of a stent according to a second example embodiment of the present invention, wherein a circuit portion 200 may be placed in the exterior thereof. FIG. 4 is a cross-sectional view of a B-B part in FIG. 2B. As shown in FIG. 2B and FIG. 4, the circuit portion 200 may be placed on the outer surface of one side of the stent 250. Since other configurations thereof are the same as the aforementioned first example embodiment, description therefor is omitted herein.

Figure 5:
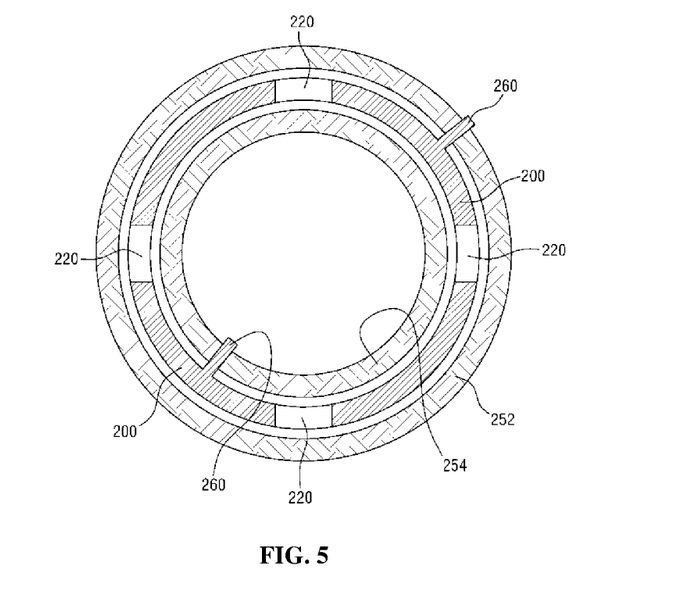
FIG. 5 is a cross-sectional view of a stent according to a third example embodiment of the present invention, wherein a circuit portion is placed in a mid-point of a cross-sectional surface thereof.

FIG. 5 is a cross-sectional view of a stent according to a third example embodiment of the present invention, wherein a circuit portion 200 may be placed in a mid-point of a cross-sectional surface thereof. As shown in FIG. 5, the circuit portion 200 may be placed between an outer stent 252 and an inner stent 254. A double concentric structure of FIG. 5 may be applied to either the whole length of the stent 250 or the only region where the circuit portion 200 is placed. The circuit portion 200 may be embodied by using ASIC, MEMS or a One Chipped IC chip together with a Flexible Printed Circuit Board (FPCB) in a manner of bending to be round. A plurality of the LEDs 220 may be exposed to the surroundings of the circuit portion 200, and the sensor 260 may be exposed to a desired position (for example: the inner or outer side of the stent). Even though not shown in FIG. 5, the circuit portion 200 may be coated with a silicone layer 280.

Figure 6D:
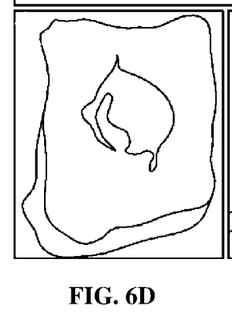
Figure 6E:
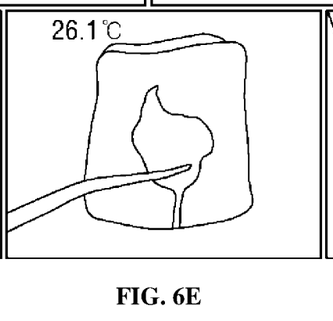
Figure 6F:
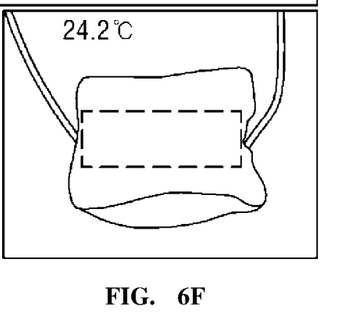

FIGS. 6A-6F show photographs of a heating stent according to one example embodiment of the present invention and of various heating experiments. FIG. 6A shows a mono layered heating stent and FIG. 6B shows a double layered heating stent. FIG. 6C is the photograph of a heating stent in a heated state, taken using an infrared camera, in which the heating stent is heated by coupling electrodes to both ends thereof and applying an electric current thereto. FIGS. 6D-6F are infrared photographs showing a heating process in which a stent is inserted into a variety of tissues and generates heat.

Further, FIGS. 7A-7E show graphs which indicate correlation between power and temperature obtained through the heating experiments according to FIGS. 6A-6F. The horizontal axis on the graph indicates power (W) and the vertical axis thereon indicates average temperature (° C.). As shown in FIGS. 7A-7E, the temperature and the power are in the linear relationship which is capable of being represented by a linear function.

Figure 7A:
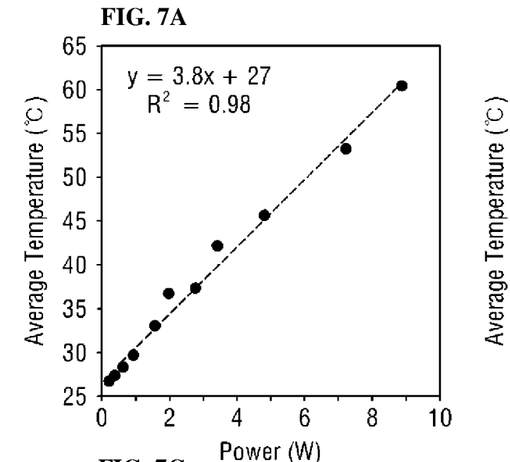
FIGS. 7A-7E show graphs which indicate correlation between power and temperature obtained through the heating experiments according to FIGS. 6A-6F.
Figure 7B:
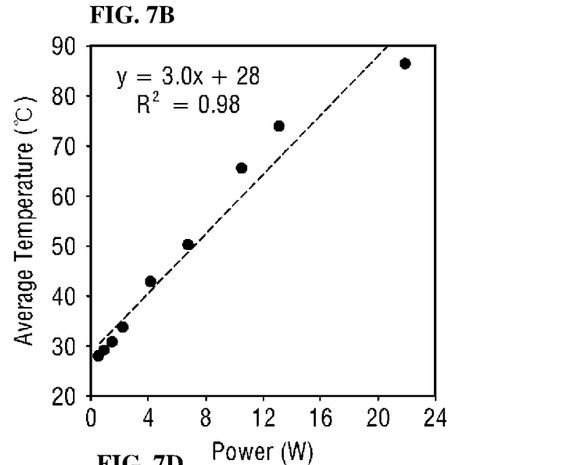
Figure 7C:
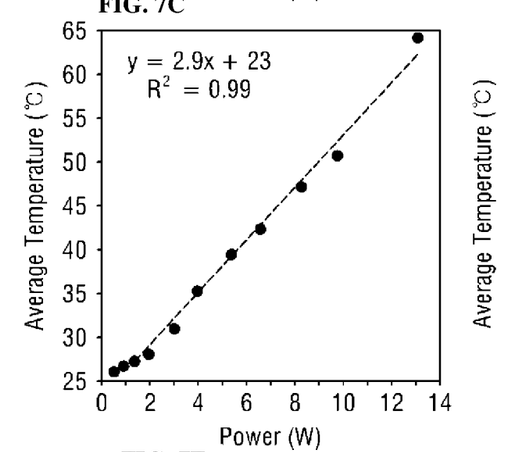
Figure 7D:
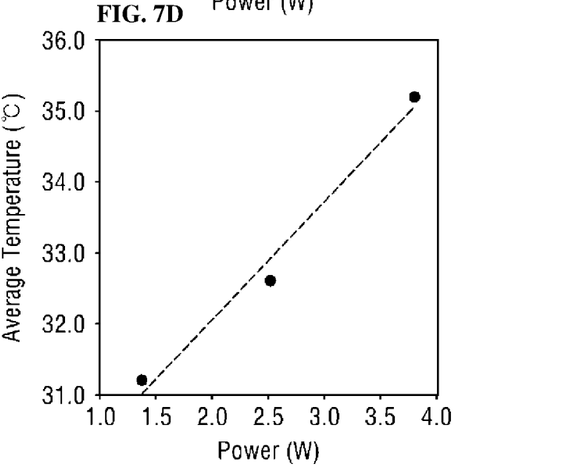
Figure 7E:
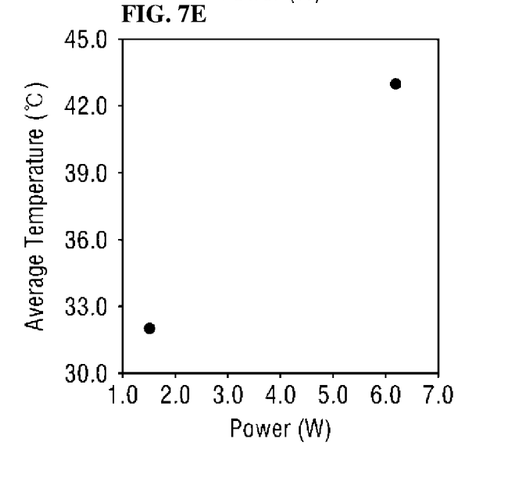

More particularly, FIG. 7A is the graph of an experiment for a mono layered heating stent. FIG. 7B is the graph of an experiment for a double layered heating stent. FIG. 7C is the graph of an experiment for a double layered heating stent inserted into a tissue. FIG. 7D is the graph of an experiment for a mono layered mesh heating stent (the negative is coupled to the center). FIG. 7E is the graph of an experiment for a mono layered mesh heating stent (the negative is coupled to center with a thicker wire).

The first control portion 100 may amplify an RF signal to corresponding power to generate desired temperature heat, based on such graphs. For example, the mono layered stent of FIG. 6A may need 4-5 W of power for 3-5 seconds in order to reach 45° C.-50° C. of temperatures which are adapted for necrosis of the cancer cell. The double layered stent of FIG. 6B may need 6-7 W of power.

Even though the present invention is described in connection with the aforementioned example embodiments, it would be understood by those skilled in the art that various modifications and alternations may be made within the purport and scope of the present invention. Further, it is obvious that such modifications and alternations belong the scope of the claimed invention.

What is claimed is:

1. A stent having terminal ends and being coated with a photosensitizer, the stent comprising:
   a circuit comprising:
      a light emitting diode configured to emit a predetermined wavelength of light;
      a power receiving portion for wirelessly receiving radio frequency power from a power transmitting portion of an external operating apparatus, and for converting the radio frequency power to electric power;
      a power storage portion for storing the electric power converted by the power receiving portion, and for providing stored power as the electric power to the circuit;
      a second communication portion for wirelessly receiving a control command from a first control portion via a first communication portion of the external operating apparatus;
      a second control portion for applying, based on the control command, the electric power to terminal ends of the stent, causing an electric current to flow through the stent between the terminal ends, the flow of the electric current causing heating of the stent, and for controlling a temperature of the stent as heated in order to provide hyperthermia therapy to a tumor, the second control portion further for applying, based on the control command, the electric power to the light emitting diode to emit the predetermined wavelength of light to the photosensitizer in order to provide photodynamic therapy to the tumor;
   a nontoxic silicone layer coating at least one of the power receiving portion, the power storage portion, the second communication portion, and the second control portion, wherein the nontoxic silicone layer fixes the circuit to the stent; and
   wherein the stent comprises an outer stent and an inner stent forming a concentric structure along at least a portion of a length of the stent, and the nontoxic silicone layer is disposed in the concentric structure between the outer stent and the inner stent.

2. The stent of claim 1, wherein the circuit comprises a sensor configured to detect a biochemical environment in which the stent is inserted, wherein the second control portion is further for wirelessly transmitting an output of the sensor to the first control portion of the external operating apparatus via the second communication portion.

* * * * *